(12) United States Patent
Nemi et al.

(10) Patent No.: US 12,357,720 B2
(45) Date of Patent: Jul. 15, 2025

(54) ULTRA-VIOLET LIGHTING FIXTURE

(71) Applicant: Viscor, Inc., Toronto (CA)

(72) Inventors: Santino Nemi, Toronto (CA); Antonio Magisano, Toronto (CA); Sandu Cusmariu, Toronto (CA); Timothy Stevens, Mount Pleasant, WI (US); Song Liu, Toronto (CA)

(73) Assignee: Viscor, Inc., Toronto (CA)

( * ) Notice: Subject to any disclaimer, the term of this patent is extended or adjusted under 35 U.S.C. 154(b) by 710 days.

(21) Appl. No.: 17/740,746

(22) Filed: May 10, 2022

(65) Prior Publication Data
US 2023/0364296 A1 Nov. 16, 2023

(51) Int. Cl.
*A61L 9/20* (2006.01)
*F21S 8/02* (2006.01)
*F21V 9/06* (2018.01)
*F21Y 105/16* (2016.01)

(52) U.S. Cl.
CPC .............. *A61L 9/20* (2013.01); *F21S 8/026* (2013.01); *F21V 9/06* (2013.01); *A61L 2209/12* (2013.01); *F21Y 2105/16* (2016.08)

(58) Field of Classification Search
CPC ........ A61L 9/20; A61L 2209/12; F21S 8/026; F21V 9/06; F21Y 2105/16
See application file for complete search history.

(56) References Cited

U.S. PATENT DOCUMENTS

| | | | |
|---|---|---|---|
| 8,632,206 B2 | 1/2014 | Chung | |
| 9,937,274 B2 | 4/2018 | Clynne et al. | |
| 9,981,052 B2 | 5/2018 | Clynne et al. | |
| 10,101,005 B2 | 10/2018 | Mealey | |
| 10,960,090 B2 | 3/2021 | Clynne et al. | |
| 2021/0003317 A1* | 1/2021 | Polidoro | F21V 33/0088 |
| 2021/0008235 A1 | 1/2021 | Clynne et al. | |

FOREIGN PATENT DOCUMENTS

CA 2978469 A1 9/2016

* cited by examiner

*Primary Examiner* — Sean M Luck
(74) *Attorney, Agent, or Firm* — KDW Firm PLLC

(57) ABSTRACT

A lighting fixture arranged and configured to emit visible (e.g., white) light and ultraviolet light. In one embodiment, the lighting fixture includes one or more visible light emitting compartments and one or more ultraviolet light emitting compartments for housing the visible light emitting components and the ultraviolet light emitting compartments, respectively. A shield is positioned between the visible light emitting compartment(s) and the ultraviolet light emitting compartment(s). The shield being configured to enable the visible light to pass therethrough while prohibiting the ultraviolet light from passing therethrough. Thus arranged, the visible light is allowed to enter the ultraviolet light emitting compartment(s) and mix with the ultraviolet light, while the ultraviolet light is prevented from entering the visible light emitting compartment(s) where it may degrade the components and materials of the visible light emitting compartment(s) contained within.

20 Claims, 6 Drawing Sheets

ULTRA-VIOLET LIGHTING FIXTURE

TECHNICAL FIELD

The present disclosure is directed to lighting fixtures and, more particularly, to an improved lighting fixture arranged and configured to emit visible light and ultraviolet light.

BACKGROUND

Lighting fixtures are well known. Lighting fixtures may be used, positioned within, mounted, etc. (terms used interchangeably without the intent to limit or distinguish) in a variety of different spaces. In addition to emitting visible light, some lighting fixtures may emit ultraviolet light or ultraviolet germicidal irradiance (UV-GI) for purposes of deactivating pathogens in a space in which the lighting fixture is located.

In use, combining ultraviolet and visible light into a lighting fixture provides numerous advantages. For example, the emittance of visible light from a lighting fixture that also emits ultraviolet light allows the visible light to obscure the violet glow emitted at some UV-GI wavelengths. In addition, the fluorescence caused when some materials are exposed to UV-GI wavelengths may also be obscured.

However, combining ultraviolet and visible light into a single lighting fixture has a number of disadvantages. For example, UV-GI wavelengths can cause some materials to discolor or degrade, especially at high irradiance levels. For example, the presence of ultraviolet light may cause some plastics to discolor, become brittle, and cause some paints to become flaky. To combat discoloration or degradation, precautions are required within the lighting fixture to ensure components are either manufactured from materials suitable for exposure to UV-GI, or are protected from this irradiance. In many cases, manufacturing components from materials that are suitable for exposure to UV-GI is more costly than standard materials. These components may include wire insulation, diffusers, paint finishes, solder masks for PCB boards, and plastics. One common solution to protect components used to emit visible light from exposure to UV-GI, is to cover or hide these components. However, some components cannot be hidden. As a result, these components must be manufactured from materials suitable for exposure to UV-GI. As mentioned, these materials are more costly, thereby driving up the cost of the lighting fixture.

Alternatively, in some lighting fixtures, the ultraviolet light emitting components may be separated from the visible light emitting components. That is, for example, the lighting fixture may include one or more visible light emitting compartments and one or more ultraviolet light emitting compartments in which the one or more visible light emitting compartments include the necessary components to emit visible light while the one or more ultraviolet light emitting compartments include the necessary components to emit ultraviolet light. However, by separating the lighting fixture into separate compartments for emitting visible light and ultraviolet light, in use, the ultraviolet compartment of the lighting fixture will appear to be non-operational since ultraviolet light is non-visible to the human eye. As such, consumer confusion and non-pleasing aesthetics are a common complaint.

Thus there remains a need for an improved lighting fixture designed and configured to emit both visible and ultraviolet light in a cost-effective and aesthetically pleasing manner. It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a lighting fixture arranged and configured to emit visible (e.g., white) light and ultraviolet light in a single fixture. In one embodiment, the lighting fixture separates the UV-GI emitting components from the visible light emitting components, and provides a method for combining the visible illumination with the UV-GI within a specified area or compartment of the lighting fixture. As a result, the lighting fixture is arranged and configured to emit both visible light and ultraviolet light without the appearance of dead zones, or non-working or non-light emitting zones, while ensuring components and materials not located in the UV-GI emitting compartments, are protected from ultraviolet exposure (e.g., components and materials which are not suitable for exposure to UV-GI, remain separated and protected).

In one embodiment, the lighting fixture includes one or more visible light emitting compartments and one or more ultraviolet light emitting compartments, wherein the visible light emitting compartment(s) includes the visible light emitting components while the ultraviolet light emitting compartment(s) includes the ultraviolet light emitting components. The lighting fixture further including one or more shields within the fixture for separating the visible light emitting compartment(s) (e.g., visible light components) from the ultraviolet light emitting compartment(s) (e.g., UV-GI components). In use, the shield(s) is arranged and configured to enable visible wavelengths to pass therethrough while preventing ultraviolet transmission. That is, in one embodiment, the shield(s) is arranged and configured to absorb or reflect UV-GI wavelengths. Thus arranged, in use, the shield(s) enables the visible light to be transmitted from the visible light emitting compartment(s) through the shield and into the ultraviolet light emitting compartment(s) where it may be combined with the ultraviolet light and emitted from the ultraviolet light emitting compartment(s) of the lighting fixture into the space. Meanwhile, the ultraviolet light from the ultraviolet light emitting compartment(s) is prevented from entering into the visible light emitting compartment(s) where it may interact and damage the visible light emitting components. As such, the lighting fixture allows visible light to combine with the UV-GI in a specified area (e.g., ultraviolet light emitting compartment or ultraviolet chamber) of the lighting fixture, while protecting components and materials used in the rest of the lighting fixture.

In one embodiment, the shield may be a transparent shield. Alternatively, the shield may be semi-transparent, translucent, or the like.

In one embodiment, a lighting fixture arranged and configured to emit ultraviolet light and visible light is disclosed. The lighting fixture including an enclosure including one or more visible light emitting compartments and one or more ultraviolet light emitting compartments; visible light emitting components positioned within the one or more visible light emitting compartments; ultraviolet light emitting components positioned within the one or more ultraviolet light emitting compartments; and one or more shields arranged and configured to enable the visible light to pass therethrough so that the visible light travels from the one or more visible light emitting compartments to the one or more ultraviolet light emitting compartments, the one or more shields arranged and configured to prohibit the ultraviolet light from passing therethrough so that the ultraviolet light is prevented from traveling from the one or more ultraviolet light emitting compartments to the one or more visible light emitting compartments.

In one embodiment, the one or more shields prevent the transmission of ultraviolet light into the one or more visible light emitting compartments to protect material and components found within the one or more visible light emitting compartments from degradation, discoloration, or a combination thereof.

In one embodiment, the lighting fixture further includes a first lens positioned over the one or more visible light emitting compartments arranged and configured to enable the visible light to pass therethrough and a second lens positioned over the one or more ultraviolet light emitting compartments arranged and configured to enable visible and ultraviolet light to pass therethrough.

In one embodiment, when activated, the first and second lens appear entirely illuminated with visible light.

In one embodiment, the ultraviolet light is arranged and configured to deactivate pathogens in a space in which the lighting fixture is located.

In one embodiment, the shield is a transparent shield.

In one embodiment, the shield is selected from a group consisting of an acrylic, a glass, and a polymeric.

In one embodiment, the shield is manufactured from a polycarbonate.

In one embodiment, the ultraviolet light emitting components are continuously ON.

In one embodiment, the visible light emitting components are controllable via a switch, a motion sensor, or a combination thereof.

In one embodiment, the one or more visible light emitting compartments include first and second visible light emitting compartments; the one or more ultraviolet light emitting compartments include an ultraviolet light emitting compartment; and the one or more shields includes first and second shields; wherein the ultraviolet light emitting compartment is positioned in-between the first and second visible light emitting compartments with the first shield positioned on a first side of the ultraviolet light emitting compartment and the second shield is positioned on a second side of the ultraviolet light emitting compartment.

In one embodiment, a lighting fixture arranged and configured to emit ultraviolet light and visible light is disclosed. The lighting fixture including an enclosure including a visible light emitting compartment and an ultraviolet light emitting compartment; visible light emitting components positioned within the visible light emitting compartment; ultraviolet light emitting components positioned within the ultraviolet light emitting compartment; and a shield arranged and configured to enable the visible light to pass therethrough so that the visible light travels from the visible light emitting compartment to the ultraviolet light emitting compartment, the shield arranged and configured to prohibit the ultraviolet light from passing therethrough so that the ultraviolet light is prevented from traveling from the ultraviolet light emitting compartment to the visible light emitting compartment.

In one embodiment, the shield prevents the transmission of ultraviolet light into the visible light emitting compartment to protect material and components found within the visible light emitting compartment from degradation, discoloration, or a combination thereof.

In one embodiment, the lighting fixture further includes a first lens positioned over the visible light emitting compartment arranged and configured to enable the visible light to pass therethrough and a second lens positioned over the ultraviolet light emitting compartment arranged and configured to enable visible and ultraviolet light to pass therethrough.

In one embodiment, when activated, the first and second lens appear entirely illuminated with visible light.

In one embodiment, the ultraviolet light is arranged and configured to deactivate pathogens in a space in which the lighting fixture is located.

In one embodiment, the ultraviolet light emitting components are continuously ON.

In one embodiment, the visible light emitting components are controllable via a switch, a motion sensor, or a combination thereof.

In one embodiment, the shield is selected from a group consisting of an acrylic, a glass, and a polymeric.

In one embodiment, the shield is manufactured from a polycarbonate.

BRIEF DESCRIPTION OF THE DRAWINGS

By way of example, a specific embodiment of the disclosed device will now be described, with reference to the accompanying drawings, in which.

Figure 1:
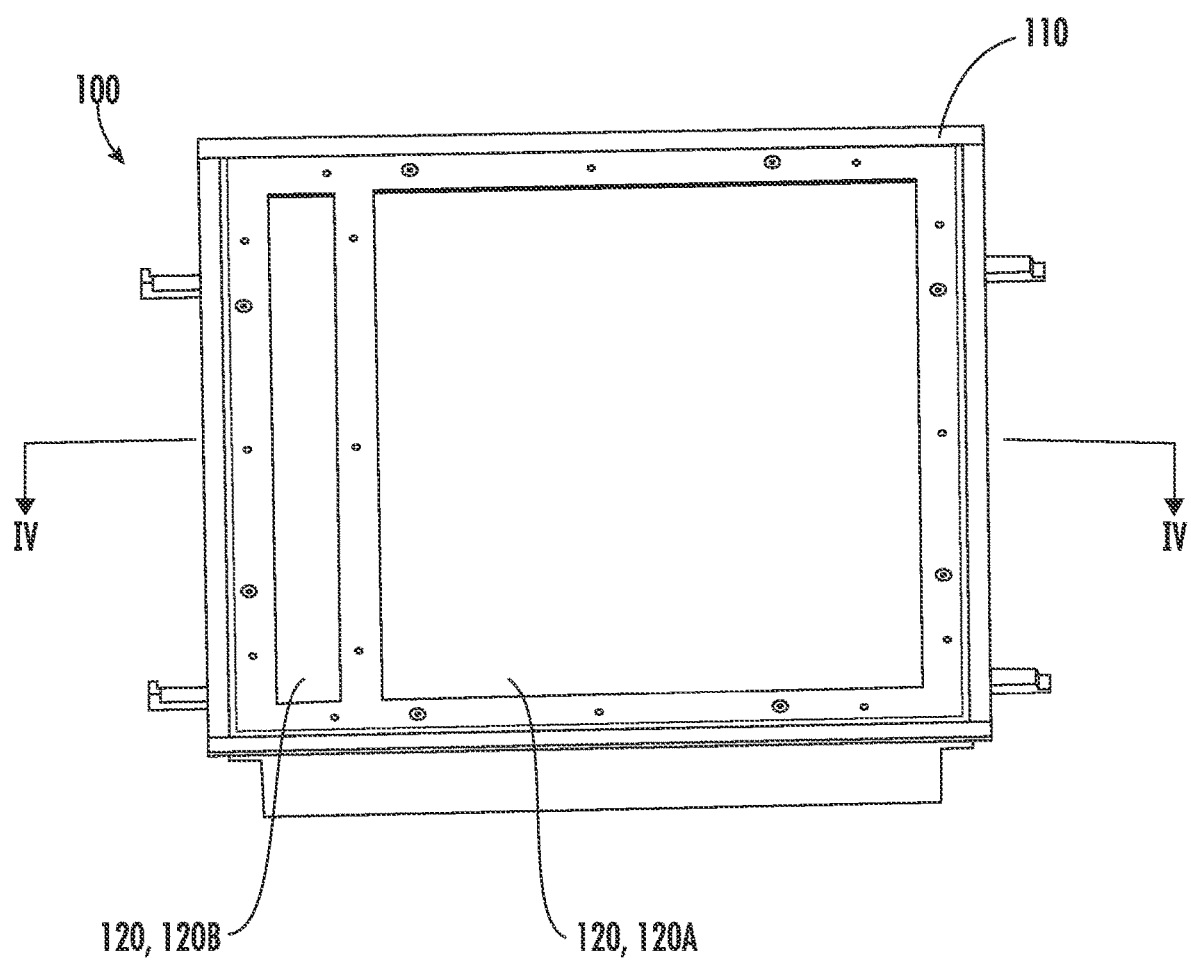
FIG. 1 illustrates a view of an example embodiment of a lighting fixture in accordance with one or more features of the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of a lighting fixture arranged and configured to emit visible (e.g., white) light and ultraviolet light will now be described more fully hereinafter with reference to the accompanying drawings, in which one or more features of the lighting fixture will be shown and described. It should be appreciated that the various features may be used independently of, or in combination, with each other. It will be appreciated that the lighting fixture may be embodied in many different forms and should not be construed as being limited to the embodiments set forth herein.

Rather, these embodiments are provided so that this disclosure will convey certain features of the lighting fixture to those skilled in the art.

Ultraviolet light emission or ultraviolet germicidal irradiance (UV-GI) is known. In use, the transmission of ultraviolet light may be used to deactivate pathogens in a space or area. However, providing a single lighting fixture with both visible light emission and ultraviolet light emission creates a number of challenges. For example, the presence of ultraviolet light may degrade or discolor some materials. That is, for example, incorporation of ultraviolet light into a lighting fixture may damage certain materials used to provide the visible light. To compensate for this, either the visible light emitting components must be manufactured from high-grade materials able to withstand exposure to ultraviolet light, or the visible light emitting components must be separated or protected from the ultraviolet light. Manufacturing visible light emitting components from high-grade materials able to withstand exposure to ultraviolet light may significantly increase the cost of the lighting fixture. Alternatively, separating the visible light from the ultraviolet light may cause the creation of a dead zone in the lighting fixture. That is, an area or portion of the lighting fixture may appear non-operational to end users since ultraviolet light is not visible to end users, causing the area or portion of the lighting fixture emitting ultraviolet light to appear black or non-operational.

In accordance with one or more features of the present disclosure, the lighting fixture or luminaire (terms used interchangeably herein without the intent to limit or distinguish) is arranged and configured to emit visible (e.g., white) light and ultraviolet light. As such, a single lighting fixture is arranged and configured to emit both visible and ultraviolet light. In particular, in accordance with one or more features of the present disclosure, the lighting fixture separates the ultraviolet light emitting components from the visible light emitting components. For example, in one embodiment, the lighting fixture may include one or more visible light emitting compartments and one or more ultraviolet light emitting compartments. The visible light emitting components may be located in, positioned, etc. within the visible light emitting compartment(s). The ultraviolet light emitting components may be located in, positioned, etc. in the ultraviolet light emitting compartment(s). A shield, such as, for example, a transparent shield, arranged and configured to enable, allow, etc. the visible light to pass therethrough while prohibiting, preventing, etc. the ultraviolet light from passing therethrough may be positioned between the visible light emitting compartment(s) and the ultraviolet light emitting compartment(s). Thus arranged, the visible light, in addition to being emitted from the visible light emitting compartment(s) of the lighting fixture directly into the space, may travel into the ultraviolet light emitting compartment(s) where it combines with the ultraviolet light before being emitted from the ultraviolet light emitting compartment(s) directly into the space. As such, the entire lighting fixture gives the impression that light is being emitted from the entire space or enclosure of the lighting fixture. In addition, by preventing the ultraviolet light from traveling through the shield, the visible light emitting components located in the visible light emitting compartment(s) are protected from the ultraviolet light.

With reference to FIGS. 1-4, in accordance with one or more features of the present disclosure, a lighting fixture 100 arranged and configured to emit visible (e.g., white) light and ultraviolet light is shown. As illustrated, the lighting fixture 100 includes a housing or an enclosure 110 and a lens or cover 120 coupled to the enclosure 110. In use, the lens or cover 120 enables light to pass therethrough to illuminate the space. In a preferred embodiment, for reasons that will become apparent below, the lighting fixture 100 may include first and second lens or covers 120A, 120B. In one embodiment, the second lens 120B is arranged and configured to enable the passage of ultraviolet light therethrough without degrading the second lens over time. For example, in one embodiment, the second lens 120B may be manufactured from a UV-T material (e.g., ultraviolet transmissible material such as acrylic plastic configured to enable ultraviolet light to pass therethrough). The first lens 120A may be manufactured from any suitable material now known or hereafter developed.

Figure 2:
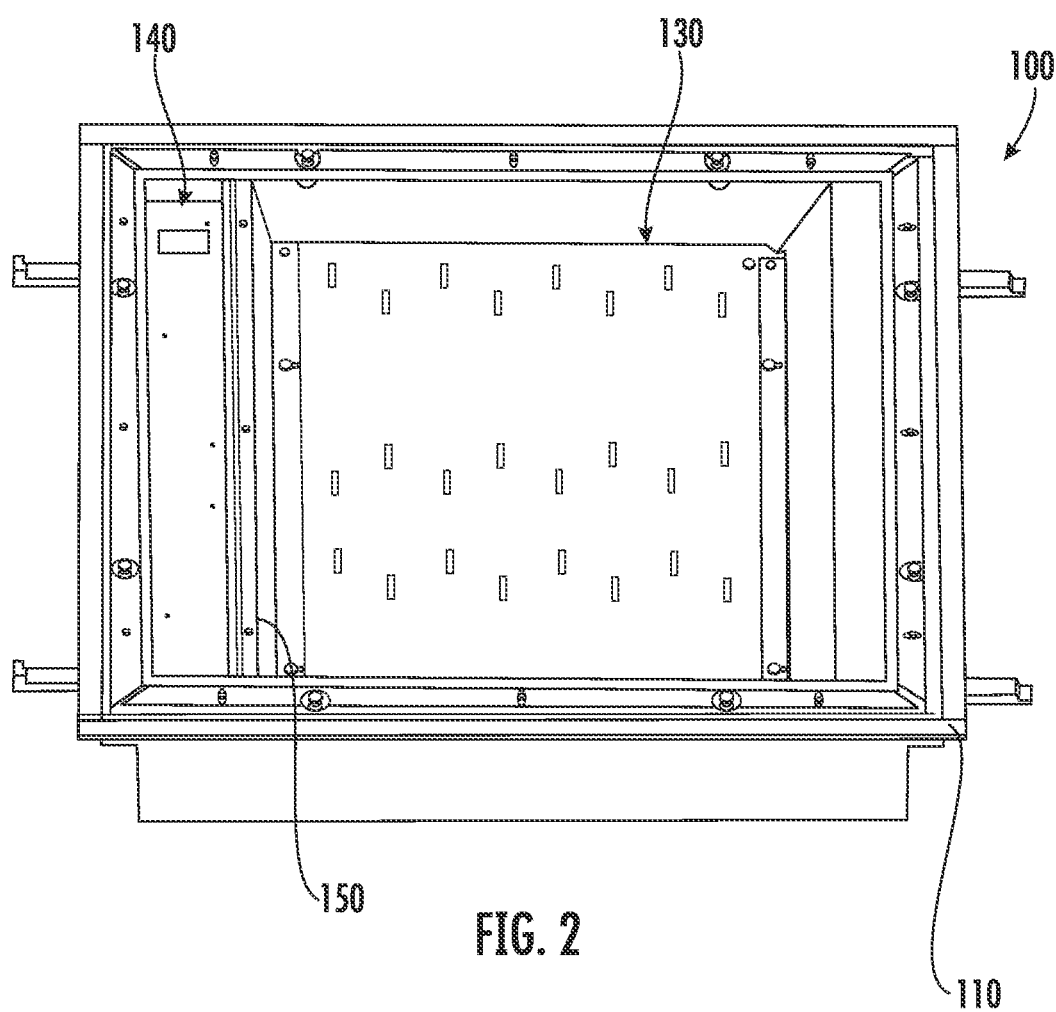
FIG. 2 illustrates a plan view of the lighting fixture in FIG. 1, the lighting fixture shown with the cover or lens removed.
Figure 3:
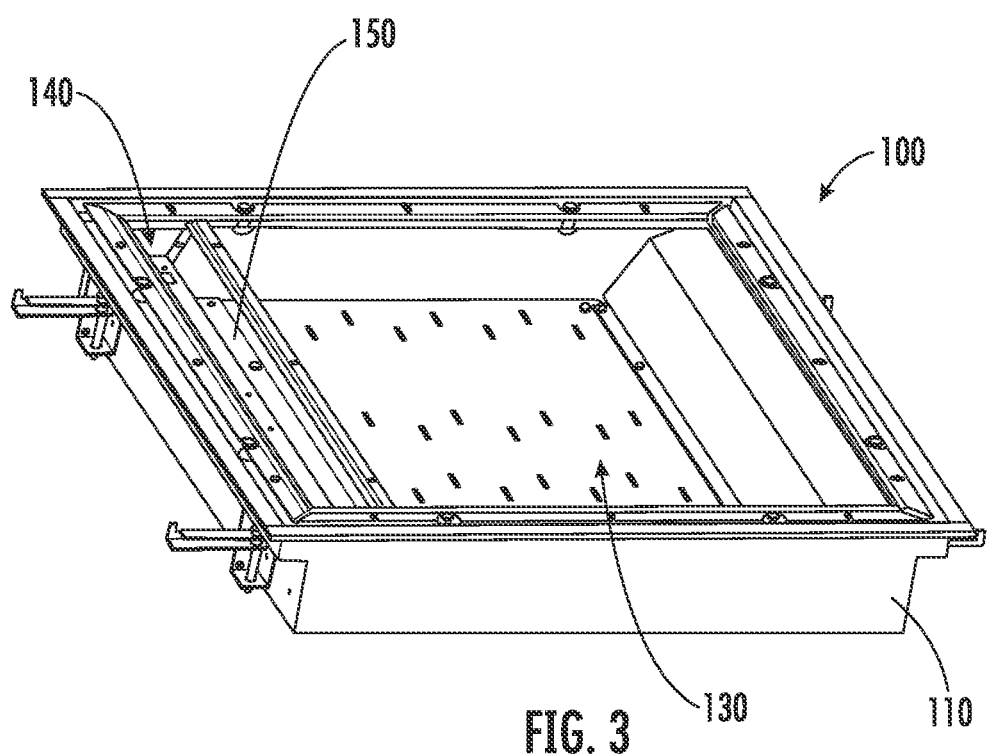
FIG. 3 illustrates an alternate view of the lighting fixture in FIG. 1, the lighting fixture shown with the cover or lens removed.
Figure 4:
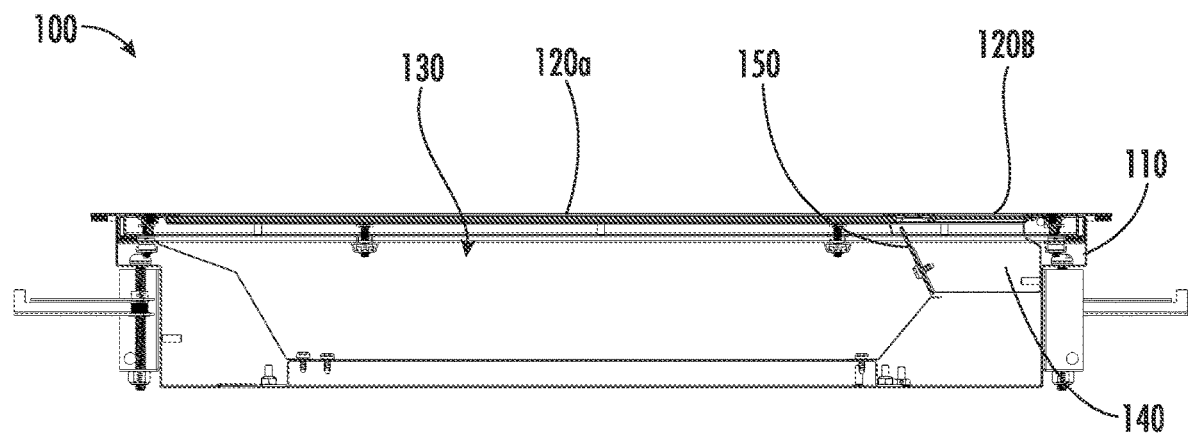
FIG. 4 illustrates a cross-sectional view of the lighting fixture shown in FIG. 1, taken along line IV-IV in FIG. 1.

As best shown in FIGS. 2-4, the lighting fixture 100 includes a visible light emitting compartment 130 and an ultraviolet light emitting compartment 140. A shield 150 is positioned between the visible light emitting compartment and the ultraviolet light emitting compartment 130, 140. In one embodiment, as illustrated, the shield 150 extends the entire width and height of the enclosure between the visible light emitting compartment and the ultraviolet light emitting compartment 130, 140, although other configurations are envisioned. In use, the visible light emitting compartment 130 includes visible light emitting components. For example, in use, the visible light emitting compartment 130 may be arranged and configured to include light emitting diodes (LEDs) and corresponding circuitry needed to emit visible light. Alternatively, the visible light emitting compartment 130 may include any now known or hereafter developed visible light emitting components including, for example, fluorescent lights.

In use, the ultraviolet light emitting compartment 140 includes ultraviolet light emitting components. For example, in use, the ultraviolet light emitting compartment 140 may be arranged and configured so that ultraviolet light components contained therein emit ultraviolet light arranged and configured to reduce harmful bacteria on surfaces located in the space in which the lighting fixture 100 is mounted. The ultraviolet light emitting components may be any now known or hereafter developed lighting technology configured to emit ultraviolet light. For example, in one embodiment, the ultraviolet light emitting components may be arranged and configured to emit 365 nm ultraviolet light. Alternatively however, the ultraviolet light emitting components may be arranged and configured to emit wavelengths between 315 nm to 400 nm, preferably 365 nm to 395 nm such as, for example, wavelengths of 377 nm or 395 nm ultraviolet light.

In accordance with one or more features of the present disclosure, the shield 150 is arranged and configured as a transparent shield, although this is but one configuration and the shield 150 may be semi-transparent, translucent, etc. In use, the shield 150 is arranged and configured to permit, enable, etc. the visible light from the visible light emitting components in the visible light emitting compartment 130 to pass through the shield 150 and into the ultraviolet light emitting compartment 140. The shield 150 is also arranged and configured to prevent, prohibit, etc. the ultraviolet light from the ultraviolet light emitting components in the ultraviolet light emitting compartment 140 from passing through the shield 150 into the visible light emitting compartment 130. Thus arranged, the visible light emitting components in the visible light emitting compartment 130 are protected from the ultraviolet light. Meanwhile, the visible light from the visible light emitting compartment 130 is permitted to enter the ultraviolet light emitting compartment 140 where it mixes with the ultraviolet light before being emitted through the lens 120 (e.g., second lens 120B). As such, the shield 150 prevents the ultraviolet light from entering the visible light chamber (e.g., visible light emitting compartment 130), allows the visible light to enter the ultraviolet chamber (e.g., ultraviolet light emitting compartment 140), all while fully illuminating the lighting fixture (e.g., visible light is allowed to pass through the first lens or cover 120A and into the space, and also allowed to pass through the shield 150 where it mixes with the ultraviolet light before passing through the second lens or cover 120B and into the space).

In use, the shield 150 may be manufactured from any suitable material arranged and configured to permit visible light to pass through but which prevents or blocks the passage of ultraviolet light. In one embodiment, the shield may be manufactured from an acrylic, a polycarbonate, a glass, a polymeric, or the like.

Figure 5A:
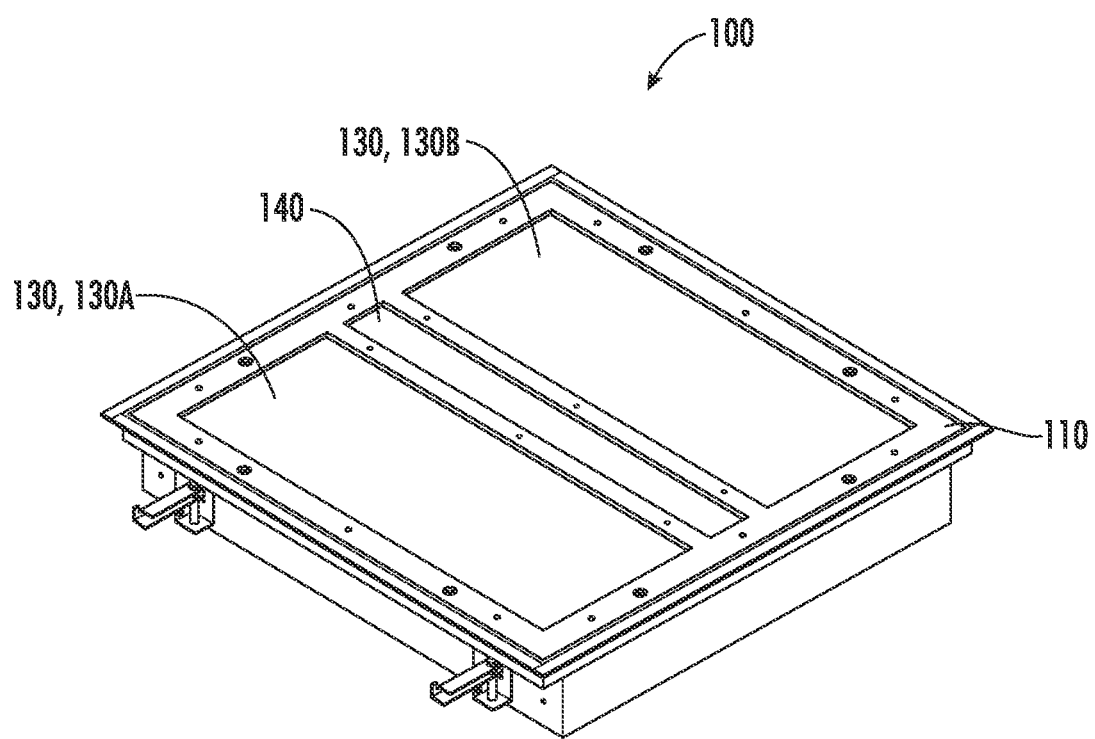
FIGS. 5A and 5B illustrate various views of an alternate example embodiment of a lighting fixture in accordance with one or more features of the present disclosure.
Figure 5B:
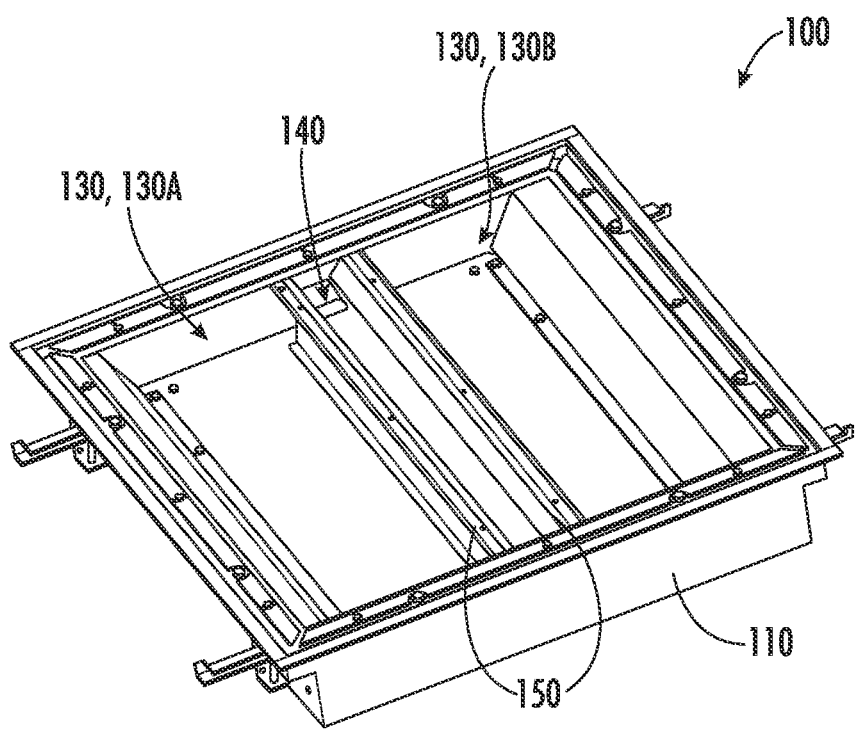

It should be appreciated that while a lighting fixture has been shown and described as including a single visible light emitting compartment and a single ultraviolet light emitting compartment, the present disclosure should not be so limited. For example, it is envisioned that multiple ultraviolet light emitting compartments may be used on either side of a single visible light emitting compartment. Alternatively, as illustrated in FIGS. 5A and 5B, it is envisioned that a single ultraviolet light emitting compartment 140 may be used in-between multiple visible light emitting compartments 130 (e.g., as illustrated, the ultraviolet compartment 140 may be centrally located in-between first and second visible light compartments 130A, 130B with a shield 150 positioned on both sides of the ultraviolet compartment 140). Moreover, it is envisioned that multiple visible light emitting compartments and multiple ultraviolet light emitting compartments may be used. As such, the present disclosure should not be limited to any particular type or arrangement of lighting fixture unless explicitly claimed.

In use, the lighting fixture may be controlled by any control system now known or hereafter developed. For example, in one embodiment, the lighting fixture may be controlled via a wired connection or a wireless connection. In one embodiment, the lighting fixture including both the visible light emitting components and the ultraviolet lighting emitting components may be controlled via a switch arranged and configured to turn the lighting fixture ON, OFF, DIM UP (increase light intensity), DIM DOWN (decrease light intensity), etc. Alternatively, the lighting fixture may be arranged and configured to be controlled via a motion sensor. In one preferred embodiment, the ultraviolet light emitting components may be continuously ON so that ultraviolet light is being emitted into the space continuously. Meanwhile, the visible light may be controlled via convenient mechanisms such as, an electrical switch, a motion sensor, or a combination thereof. In addition, and/or alternatively, the ultraviolet light may be controlled via convenient mechanisms such as, an electrical switch, a motion sensor, or a combination thereof.

Thus arranged, in accordance with one or more features of the present disclosure, a lighting fixture is provided for emitting visible and ultraviolet light. In use, the visible light emitting components are separated from the ultraviolet light emitting components to protect the visible light emitting components from degradation thereby enabling standard visible light emitting components to be utilized in the lighting fixture. For example, by preventing the ultraviolet light from entering the visible light emitting compartment standard lighting materials for the first lens, paint, etc. can be utilized to produce visible light.

In addition, the lighting fixture provides a shield that enables the visible light to enter the ultraviolet light chamber so that the ultraviolet and visible light can be mixed together and emitted through the second lens. As such, the lighting fixture is arranged and configured to be fully illuminated. In addition, the emittance of the visible light along with the ultraviolet light obscures the violet glow emitted at some ultraviolet wavelengths, and obscuring the fluorescence caused when some materials are exposed to ultraviolet wavelengths.

The foregoing description has broad application. While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art. Unless otherwise defined, all technical terms used herein have the same meaning as commonly understood by one of ordinary skill in the art to which the disclosure belongs.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counterclockwise) and the like may have been used herein. Such directional references are only used for identification purposes to aid the reader's understanding of the present disclosure. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

What is claimed is:

1. A lighting fixture arranged and configured to emit ultraviolet light and visible light, the lighting fixture comprising:
an enclosure including one or more visible light emitting compartments and one or more ultraviolet light emitting compartments;
visible light emitting components positioned within the one or more visible light emitting compartments;
ultraviolet light emitting components positioned within the one or more ultraviolet light emitting compartments; and
one or more shields arranged and configured to enable the visible light to pass therethrough so that the visible light travels from the one or more visible light emitting compartments to the one or more ultraviolet light emitting compartments, the one or more shields arranged and configured to prohibit the ultraviolet light from passing therethrough so that the ultraviolet light is prevented from traveling from the one or more ultraviolet light emitting compartments to the one or more visible light emitting compartments.

2. The lighting fixture of claim 1, wherein the one or more shields prevent the transmission of ultraviolet light into the one or more visible light emitting compartments to protect material and components found within the one or more visible light emitting compartments from degradation, discoloration, or a combination thereof.

3. The lighting fixture of claim 1, further comprising a first lens positioned over the one or more visible light emitting compartments arranged and configured to enable the visible light to pass therethrough and a second lens positioned over the one or more ultraviolet light emitting compartments arranged and configured to enable visible and ultraviolet light to pass therethrough.

4. The lighting fixture of claim 3, wherein, when activated, the first and second lens appear entirely illuminated with visible light.

5. The lighting fixture of claim 1, wherein the ultraviolet light is arranged and configured to deactivate pathogens in a space in which the lighting fixture is located.

6. The lighting fixture of claim 1, wherein the shield is a transparent shield.

7. The lighting fixture of claim 1, wherein the shield is selected from a group consisting of an acrylic, a glass, and a polymeric.

8. The lighting fixture of claim 1, wherein the shield is manufactured from a polycarbonate.

9. The lighting fixture of claim 1, wherein the ultraviolet light emitting components are continuously ON.

10. The lighting fixture of claim 9, wherein the visible light emitting components are controllable via a switch, a motion sensor, or a combination thereof.

11. The lighting fixture of claim 1, wherein:
the one or more visible light emitting compartments include first and second visible light emitting compartments;
the one or more ultraviolet light emitting compartments include an ultraviolet light emitting compartment; and
the one or more shields includes first and second shields;
wherein the ultraviolet light emitting compartment is positioned in-between the first and second visible light emitting compartments with the first shield positioned on a first side of the ultraviolet light emitting compartment and the second shield is positioned on a second side of the ultraviolet light emitting compartment.

12. A lighting fixture arranged and configured to emit ultraviolet light and visible light, the lighting fixture comprising:
an enclosure including a visible light emitting compartment and an ultraviolet light emitting compartment;

visible light emitting components positioned within the visible light emitting compartment;

ultraviolet light emitting components positioned within the ultraviolet light emitting compartment; and a shield arranged and configured to enable the visible light to pass therethrough so that the visible light travels from the visible light emitting compartment to the ultraviolet light emitting compartment, the shield arranged and configured to prohibit the ultraviolet light from passing therethrough so that the ultraviolet light is prevented from traveling from the ultraviolet light emitting compartment to the visible light emitting compartment.

13. The lighting fixture of claim 12, wherein the shield prevents the transmission of ultraviolet light into the visible light emitting compartment to protect material and components found within the visible light emitting compartment from degradation, discoloration, or a combination thereof.

14. The lighting fixture of claim 12, further comprising a first lens positioned over the visible light emitting compartment arranged and configured to enable the visible light to pass therethrough and a second lens positioned over the ultraviolet light emitting compartment arranged and configured to enable visible and ultraviolet light to pass therethrough.

15. The lighting fixture of claim 14, wherein, when activated, the first and second lens appear entirely illuminated with visible light.

16. The lighting fixture of claim 12, wherein the ultraviolet light is arranged and configured to deactivate pathogens in a space in which the lighting fixture is located.

17. The lighting fixture of claim 12, wherein the ultraviolet light emitting components are continuously ON.

18. The lighting fixture of claim 17, wherein the visible light emitting components are controllable via a switch, a motion sensor, or a combination thereof.

19. The lighting fixture of claim 17, wherein the shield is selected from a group consisting of an acrylic, a glass, and a polymeric.

20. The lighting fixture of claim 17, wherein the shield is manufactured from a polycarbonate.

* * * * *